(12) United States Patent
Syvret et al.

(10) Patent No.: US 6,365,246 B1
(45) Date of Patent: Apr. 2, 2002

(54) PACKAGE FOR SAFE STORAGE OF ELECTROPHILIC FLUORINATING AGENT

(75) Inventors: Robert George Syvret, Allentown; James Joseph Hart, Fogelsville; Andrew Joseph Woytek; Frank Michael Prozonic, both of Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/162,281

(22) Filed: Sep. 29, 1998

(51) Int. Cl.⁷ .............................................. B29D 22/00
(52) U.S. Cl. ...................................... 428/35.7; 215/306
(58) Field of Search ........................ 428/35.7; 544/106; 546/193; 215/306

(56) References Cited

U.S. PATENT DOCUMENTS

| | | | |
|---|---|---|---|
| 4,935,519 A | * 6/1990 | Van Der Puy et al. | 546/13 |
| 5,264,639 A | * 11/1993 | Morikawa et al. | 570/168 |
| 5,459,267 A | * 10/1995 | Poss et al. | 544/337 |
| 5,473,065 A | * 12/1995 | Banks | 540/472 |
| 5,631,372 A | * 5/1997 | Poss et al. | 544/352 |
| 5,804,744 A | * 9/1998 | Tan et al. | 73/864.34 |

FOREIGN PATENT DOCUMENTS

CA 710299 A * 5/1965

OTHER PUBLICATIONS

National Academy of Sciences, LCSS:Hydrogen Fluoride and Hydrofluoric Acid, 1995.*
Kirk–Othmer, Encyclopedia of Chemical Technology, 4th Edition, vol. 11, pp. 358–361.*
R.E. Banks, M.K. Besheesh, S.N. Mohialdin–Khaffaf, and I. Sharif J. Chem. Soc., Perkin Tans. 1, 1996, 2069.
G.S. Lal J. Org. Chem. 1993, 58, 2791.
M. Zupan, J. Iskra, and S. Stavber Bull. Chem. Soc. Jpn. 1995, 68, 1655.
M. Zupan, M. Papez, and S. Stavber, J. Fluorine Chem. 1996, 78, 137.

* cited by examiner

*Primary Examiner*—Harold Pyon
*Assistant Examiner*—Sow-Fun Hon
(74) *Attorney, Agent, or Firm*—Mary E. Bongiorno; Geoffrey L. Chase

(57) ABSTRACT

An economical means of safely "containing" or "packaging" commercial electrophilic fluorination agents whereby these agents are readily stored and transported in a package, typically without loss of "F⁺" activity, and in a form which is readily and directly useable, i.e., in solution or a slurry. Importantly, the solution/slurry medium provides a tremendous safety margin for storage and transportation since the solution medium has an enormous ability to absorb heat (due to the latent heat of vaporization of the liquid) relative to the contained active fluorination agent.

14 Claims, 3 Drawing Sheets

PACKAGE FOR SAFE STORAGE OF ELECTROPHILIC FLUORINATING AGENT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

There is a general need in the fluorination and pharmaceutical industry for a safe and efficient means of storing, transporting and delivering electrophilic fluorination agents primarily because of the sensitivity of these agents to thermal degradation and also due to slow loss of "$F^+$" activity in the solid undiluted form at ambient conditions.

Presently, most if not all of these agents must be stored and transported under refrigerated conditions in order to avoid the serious complications that may arise if these materials would undergo self accelerating decomposition, i.e., a runaway self-propagating thermal decomposition, as well as to preserve both the quality of the "$F^+$" component. Moreover, these materials are typically handled as solids, which is less preferable in the chemical processing industry than liquids handling.

There are a few literature citations wherein the thermal stability of electrophilic fluorination agents in solution is discussed. In R. E. Banks, M. K. Besheesh, S. N. Mohialdin-Khaffaf, and I. Sharif J. Chem. Soc., Perkin Tans. 1, 1996, 2069, it is noted that "a solution of F-TEDA-BF$_4$ (5.0 mmol) in boiling acetonitrile (50 cm$^3$) loses less than 10% of its '$F^+$' transfer capability during 24 hours." F-TEDA-BF$_4$ is 1-chloromethyl-4-fluoro-1,4-diazoniabicy,clo[2.2.2]octane bis(tetrafluoroborate) (also known as Selectfluor™ agent).

However, this is not unexpected since in G.S. Lal J. Org. Chem. 1993, 58, 2791, Lal describes numerous efficient fluorinations using F-TEDA-BF$_4$ in refluxing acetonitrile for 16 hour periods, producing very good yields of the expected fluorinated products.

In M. Zupan, J. Iskra, and S. Stavber Bull. Chem. Soc. Jpn. 1995, 68, 1655, Zupan et. al. make one general statement relating to this issue wherein they claim that they "studied the stability of 1-chloromethyl-4-fluoro-1,4-diazoniabicyclo[2.2.2]octane bis(tetrafluoroborate) (F-TEDA, 1a) in methanol, water, and acetonitrile" and found "less than a three percent loss of activity occured after 24 h at room temperature."

In a subsequent paper by Zupan et al., M. Zupan, M. Papez, and S. Stavber, J. Fluorine Chem. 1996, 78, 137, the reactions of three different N-F class fluorinating agents (including F-TEDA-BF$_4$) with different solvents was studied, however incomplete or only partial data was given, and therefore, it is not possible to make quantitative conclusions based or this work. For F-TEDA-BF$_4$ they observed a loss of "$F^+$" activity of 7% in methanol, 4% in water, acetonitrile, and ethanol, and 2% in isopropanol during a 24 hour period at room temperature.

If one assumes a constant rate of degradation or loss of "$F^+$" activity of 4% per day, the data of Zupan et al. would suggest that the "$F^+$" activity of an aqueous solution of Selectfluor™ agent would be depleted to 0.2% of its initial value in 154 days. Clearly, since in Example 1 we have shown that an aqueous solution of Selectfluor™ agent loses only 7–9.5% "$F^+$" activity in a 154 day period, our results are unexpected.

According to the work of Zupan et. al. (second citation), at higher temperature (54° C.) the rate of loss of activity was significantly accelerated. While data at room temperature was reported for F-TEDA-BF$_4$ only, the stability of the two other compounds, 1-hydro(y-4-fluoro-1,4-diazoniabicyclo[2.2.2]octane bis(tetrafluoroborate) (also known as Accufluor™ or NFTh) and N-fluorobis(phenylsulfonyl)amine (also known as NFSi) was only assessed at 54° C. and compared to F-TEDA-BF$_4$ under similar conditions. In protic solvents, water and alcohols, NFTh was found to be more stable than F-TEDA-BF$_4$ with respect to loss of "$F^+$" activity. NFSi was reported to be "very stable" at 54° C.

The prior art has shown that electrophilic fluorinating agents have various stabilities in an array of solvent systems depending on the agent and the solvent. No general pattern regarding this stability or lack of stability has been suggested by the prior art regarding when such agents would be stable in a solvent and therefore desirable in a solvent. In contrast, in the present invention provides an economical means of safely "containing" or "packaging" these commercial electrophilic fluorination agents whereby these agents are readily stored, transported and delivered in a form which is readily and directly useable, i.e., in an appropriate amount of solution, in which the solution medium provides a tremendous safety margin for storage, transportation and delivery since the solution medium will be shown below to have an enormous ability to absorb heat (due to the latent heat of vaporization of the liquid) relative to the contained electrophilic fluorination agent across an array of agents and solvents, and in some instances such a package provides storage, transportation and delivery without loss of "$F^+$" activity.

BRIEF SUMMARY OF THE INVENTION

The present invention is a package for the safe containment of a quaternary nitrogen electrophilic fluorination agent, comprising:

a) a container, having a least one sealable orifice, capable of containing the quaternary nitrogen electrophilic fluorination agent and a solvent in liquid phase under ambient conditions;

b) a quantity of the quaternary nitrogen electrophilic fluorination agent; and c) a solvent, compatible with the quaternary nitrogen electrophilic fluorination agent, in sufficient quantity to absorb the heat of decomposition of the quantity of quaternary nitrogen electrophilic fluorination agent.

Preferably, the quaternary nitrogen electrophilic fluorination agent is selected from the group consisting of: 1-chloromethyl-4-fluoro-1,4-diazoniabicyclo[2.2.2]octane bis(tetrafluoroborate); 1-chloromethyl-4-fluoro-1,4-diazoniabicyclo[2.2.2]octane fluoride (tetrafluoroborate); 1-fluoro4-hydroxy-1,4-diazoniabicyclo[2.2.2]octane bis (tetrafluoroborate); 1-fluoro-4-methyl-1,4-diazoniabicyclo[2-2-2]octane bis(tetrafluoroborate); 1-fluoro-quinuclidinium triflate; 1-fluoro-pyridinium pyridine heptafluorodiborate; 1-fluoro-pyridinium tetrafluoroborate; 1-fluoro-pyridinium triflate; 1-fluoro-2,6-dichloropyridiinium tetrafluoroborate; 1,1'-difluoro-2,2'-bipyridinium bis(tetrafluoroborate) and mixtures thereof.

Preferably, the solvent is water for non-pyridinium fluorinating agents. More preferably, the solvent includes an organic solvent. Still more preferably, the organic solvent is selected from the group consisting of: acetonitrile, propionitrile, methanol, ethanol, propanol, isopnrpanol, N,N-dimethylformamide, tetrahydrofuran, ethyl ether, aromatic hydrocarbon of $C_{u-v}$, halogenated hydrocarbon of $C_{w-x}$, and perfluorinated hydrocarbon of $C_{y-z}$. For pyridinium based fluorinating agents the solvent is preferably an organic solvent.

Alternatively, the solvent is a mixture of acetonitrile and methanol.

In a preferred embodiment, the quaternary nitrogen electrophilic fluorination agent is 1-chloromethyl-4-fluoro-1,4-diazoniabicyclo[2.2.2]octane bis(tetrafluoroborate) and the solvent is water. More preferably in this embodiment, the solvent is at least 30 wt. % water and an organic solvent selected from the group consisting of: acetonitrile; tetrahydrofuran; N,N-dimethylformamide and mixtures thereof.

Alternatively, the quaternary nitrogen electrophilic fluorination agent is 1-chloromethyl-4-fluoro-1,4-diazoniabicyclo[2.2.2]octane bis(tetrafluoroborate) and the solvent is acetonitrile and methanol.

In another alternative embodiment, the quaternary nitrogen electrophilic fluorination agent is 1-fluoro-4-hydroxy-1,4-diazoniabicyclo[2.2.2]octane bis(tetrafluoroborate) and the solvent is water. More preferably, the solvent is at least 40 wt. % water, and an organic solvent selected from the group consisting of: acetonitrile; tetrahydrofuran; N,N-dirnethylformamide and mixtures thereof.

In still another alternative embodiment, the quaternary nitrogen electrophilic fluorination agent is N-fluoroquinuclidinium triflate and the solvent is water. Preferably in this embodiment, the solvent is water and an organic solvent selected from the group consisting of: acetonitrile; tetrahydrofuran; N,N-dimethylformamide and mixtures thereof.

The present invention is also a process for safely packaging a quaternary nitrogen electrophilic fluorination agent in a container, comprising:

a) providing a container, having a least one sealable orifice, capable of containing the quaternary nitrogen electrophilic fluorination agent and a solvent in liquid phase under ambient conditions;

b) introducing a quantity of the quaternary nitrogen electrophilic fluorination agent into the container; and c) introducing a solvent, compatible with the quaternary nitrogen electrophilic fluorination agent in sufficient quantity to absorb the heat of decomposition of the quantity of quaternary nitrogen electrophilic fluorination agent, into the container.

DETAILED DESCRIPTION OF THE INVENTION

Figure 1:
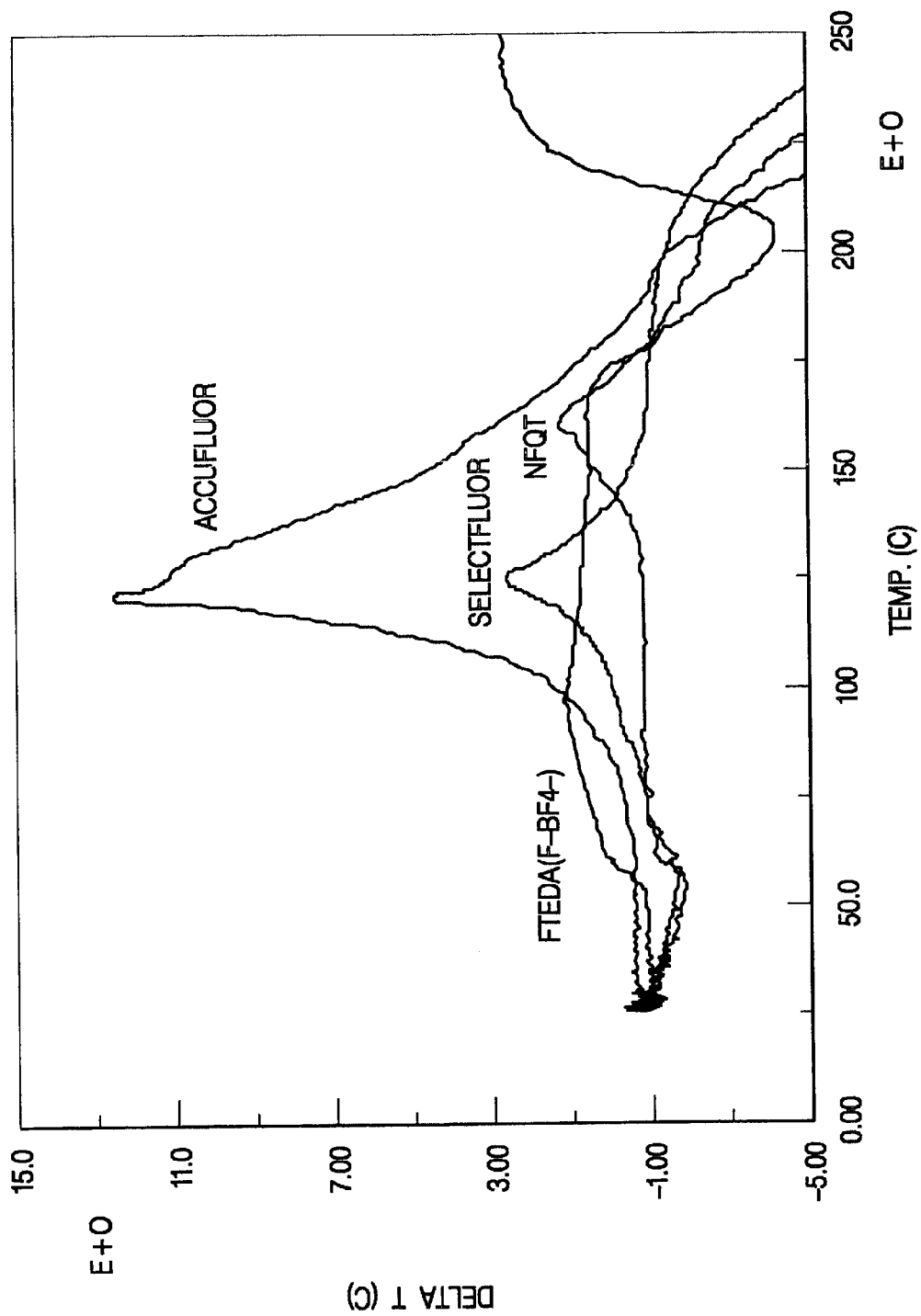
FIG. 1 is a graph of delta T in degrees celsius as temperature is ramped in degrees celsius for several fluorinating agents.

The present invention relates to a novel "package" and "process" for the safe and cost effective storage, transport, and delivery of an electrophilic fluorination agent comprising a mixture of an electrophilic fluorination agent in a solvent, such as an aqueous medium, which may contain an organic solvent.

The electrophilic fluorination agents are exemplified by, but not limited to, the quaternary nitrogen electrophilic fluorination agents: 1-chloromethyl-4-fluoro-1,4-diazoniabicyclo[2.2.2]octane bis(tetrafluoroborate); 1-chloromethyl-4-fluoro-1,4-diazoniabicyclo[2.2.2]octane fluoride (tetrafluorobo rate); 1-fluoro-4-hydroxy-l 1,4-diazoniabicyclo[2.2.2]octane bis(tetrafluoroborate); 1-fluoro-4-methyl-1, 4-diazoniabicyclo[2-2-2]octane bis (tetrafluoroborate); N-fluoro-quinuclidinium triflate; 1-fluoro-pyridinium pyridine heptafluorodiborate; 1-fluoro-pyridinium tetrafluoroborate; 1-fluoro-pyridinium triflate; 1-fluoro-2,6-dichloropyridinium tetrafluoroborate; 1,1'-difluoro-2,2'-bipyridinium bis(tetrafluoroborate) and mixtures thereof.

Preferably, the solvent is water for the non-pyridinium fluorinating agents. More preferably, the water solvent includes an organic solvent. Still more preferably, the organic solvent is selected from the group consisting of: acetonitrile, propionitrile, methanol, ethanol, propanol, isopropanol, N,N-dimethylformamide, tetrahydrofuran, ethyl ether, aromatic hydrocarbon of $C_{u-v}$, halogenated hydrocarbon of $C_{w-x}$, and perfluorinated hydrocarbon of $C_{y-z}$ where u=3, v=10 (preferably =4, v=6), w=1, x=8 (preferably w=3, x=6), y=1 and z=8(preferably 3, z=6).

Alternatively, the solvent is a mixture of acetonitrile and methanol.

For the pyridinium based fluorinating agents the solvent is preferably an organic solvent, such as those mentioned above.

Ambient conditions would typically be in the approximate range of up to 50° C., preferably up to 25° C., most preferably 0° C. to 25° C.; at pressures up to 100 psia, preferably 85 psia, most preferably 14.5. However, conditions of temperature and pressure in a closed container under appropriate pressure ratings or outfitted with pressure relief mechanisms would allow for deviations from these ranges without departing from the scope of the invention. The desirable aspect of the present invention is maintaining the solvent system under liquid phase conditions at whatever temperature and pressure conditions prevail in the container, so as to make the latent heat of vaporization available for use in the event of a rapid decomposition and resulting exotherm of the fluorination agent.

The following non-limiting examples illustrate the inability of fluorination activity in various solvents to predict the desirability and advantage of the present invention.

Examples 1–5 demonstrate the Stability of Various Electrophilic Fluorination agents in Aqueous Media. The stability of electrophilic fluorination agents can be assessed quantitatively by measuring the "$F^+$" activity as a function of time. Since degradation of an electrophilic fluorination agent is manifested in the loss of "$F^+$" activity, this analysis provides a very accurate measure of a fluorinating agents loss of efficacy with time.

In the present example, "$F^+$" activity was conveniently measured over time using the common "iodometric" method of analysis. This analysis involves addition of an excess of KI to an aqueous solution containing a known amount of a given fluorination agent. This results in a quantitative conversion of all of the "$F^+$" to $I_2$ according to eq 1.

$$F^+ + 2I^- \rightarrow I_2 + F^- \quad (1)$$

The $I_2$ is then accurately measured by careful titration with aqueous thiosulfate according to eq 2.

$$2S_2O_3^{2-}+I_2 \rightarrow S_4O_6^{2-}+2I^- \qquad (2)$$

Thus, by carefully determining the evolved iodine generated in eq 1, a measure of the "$F^+$" content can be determined. In each of the following examples, the "$F^+$" values quoted represent the average value of triplicate analysis.

EXAMPLE 1

Stability of Selectfluor™ Fluorinating Agent in Aqueous Solution

A saturated solution of commercial grade Selectfluor™ Fluorinating Agent, 1-chloromethyl-4-fluoro-1,4-diazoniabicyclo[2.2.2]octane bis(tetrafluoroborate), was prepared in $H_2O$ and stored at ambient temperature in two separate 1-L Nalgene polyethylene bottles. The "$F^+$" activity was measured initially after 14 days, and then again after 42 and 154 days at room temperature. The results are given in Table 1.

TABLE 1

Results of Iodometric Analysis of Aqueous Solutions of Selectfluor ™

| Days since Prepared | "$F^+$" titer mmol/mL | % change[a] |
|---|---|---|
| 14 days (solution 1) | 0.43 | initial |
| 14 days (solution 2) | 0.42 | initial |
| 42 days (solution 1) | 0.42 | 2.3 |
| 42 days (solution 2) | 0.45 | 0 |
| 154 days (solution 1) | 0.40 | 7.0 |
| 154 days (solution 2) | 0.38 | 9.5 | footnote
[a]Indicates percent change since initial measurement. A positive change is assigned a "0" value.

EXAMPLE 2

Stability of Accufluor™ (NFTh) Fluorinating Agent in Aqueous Solution

A solution of commercial grade Accufluor™ Fluorinating Agent (NFTh), 1-fluoro-4-hydroxy-1,4-diazoniaibicyclo[2.2.2]octane bis(tetrafluoroborate), was prepared by dissolving 20.06 g in 317.82 g of deionized $H_2O$. This sample was stored at ambient temperature in a Nalgene polyethylene bottle. The "$F^+$" activity was measured initially within 1 day of preparation, and then again after 9, 16, 24, 31, 37, and 43 days at room temperature. The results are given in Table 2.

TABLE 2

Results of Iodometric Analysis of an Aqueous Solution of Accufluor ™ (NFTh)

| Days since Prepared | "$F^+$" titer mmol/mL | % change[a] |
|---|---|---|
| within 1 day | 1.24 | initial |
| 9 days | 1.25 | 0 |
| 16 days | 1.24 | 0 |
| 24 days | 1.23 | 0.8 |
| 31 days | 1.23 | 0.8 |

TABLE 2-continued

Results of Iodometric Analysis of an Aqueous Solution of Accufluor ™ (NFTh)

| Days since Prepared | "$F^+$" titer mmol/mL | % change[a] |
|---|---|---|
| 37 days | 1.22 | 1.6 |
| 43 days | 1.21 | 2.4 | footnote
[a]Indicates percent change since initial measurement. A positive change is assigned a "0" value.

EXAMPLE 3

Stability of NFQT Fluorinating Agent in Aqueous Solution

A solution of NFQT Fluorinating Agent, N-fluoroquinuclidinium triflate, was prepared by dissolving 6.6 g in 37.25 g of deionized $H_2O$. This sample was stored at ambient temperature in a Nalgene polyethylene bottle. The "$F^+$" activity was measured initially within 1 day of preparation, and then again after 9, 16, 22, and 28 days at room temperature. The results are given in Table 3.

TABLE 3

Results of Iodometric Analysis of an Aqueous Solution of NFQT

| Days since Prepared | "$F^+$" titer mmol/mL | % change[a] |
|---|---|---|
| within 1 day | 0.55 | initial |
| 9 days | 0.53 | 3.6 |
| 16 days | 0.54 | 1.8 |
| 22 days | 0.54 | 1.8 |
| 28 days | 0.54 | 1.8 | footnote
[a]Indicates percent change since initial measurement. A positive change is assigned a "0" value.

EXAMPLE 4

Stability of Selectfluor™ Fluorinating Agent in $CH_3CN/H_2O$ Solution

A solution of commercial grade Selectfluor™ Fluorinating Agent, 1-chloromethyl-4-fluoro-1,4-diazoniabicyclo[2.2.2]octane bis(tetrafluoroborate), was prepared by dissolving 9.00 g in 44.82 g of a 50:50 (v/v) mixture of $CH_3CN/H_2O$ and stored at ambient temperature in a Nalgene polyethylene bottle. The "$F^+$" activity was measured initially within 1 day of preparation, and then again after 7, 15, 21, and 29 days at room temperature. The results are given in Table 4.

TABLE 4

Results of Iodometric Analysis of a $CH_3CN/H_2O$ Solution of Selectfluor ™

| Days since Prepared | "$F^+$" titer mmol/mL | % change[a] |
|---|---|---|
| within 1 day | 0.45 | initial |
| 7 days | 0.44 | 2.2 |
| 15 days | 0.45 | 0 |

TABLE 4-continued

Results of Iodometric Analysis of a
CH₃CN/H₂O Solution of Selectfluor ™

| Days since Prepared | "F⁺" titer mmol/mL | % change[a] |
|---|---|---|
| 21 days | 0.44 | 2.2 |
| 29 days | 0.44 | 2.2 | footnote
[a]Indicates percent change since initial measurement. A positive change is assigned a "0" value.

EXAMPLE 5

Stability of Selectfluor™ Fluorinating Agent in CH₃CN/CH₃OH Solution

A saturated solution of commercial grade Selectfluor™ Fluorinating Agent, 1-chloromethyl4-fluoro-1,4-diazoniabicyclo[2.2.2]octane bis(tetrafluoroborate), was prepared by dissolving 9.01 g in 39.26 g of a 50:50 (v/v) mixture of CH₃CN/CH₃OH and stored at ambient temperature in a Nalgene polyethylene bottle. The "F⁺" activity was measured initially within 1 day of preparation, and then again after 7, 15, 21, and 29 days at room temperature. The results are given in Table 5.

TABLE 5

Results of Iodometric Analysis of a
CH₃CN/CH₃OH Solution of Selectfluor ™

| Days since Prepared | "F⁺" titer mmol/mL | % change[a] |
|---|---|---|
| within 1 day | 0.11 | initial |
| 7 days | 0.11 | 0 |
| 15 days | 0.11 | 0 |
| 21 days | 0.10 | 9.1 |
| 29 days | 0.11 | 0 | footnote
[a]Indicates percent change since initial measurement. A positive change is assigned a "0" value.

In comparison to Examples 1–5 which show solvent stabilization of these agents, comparative Examples 6–12 demonstrate the instability of various electrophilic fluorination agents in aqueous media, and therefore the lack of a pattern or teaching that fluorination activity stability would suggest the desirability and advantage of agent/solvent packaging.

EXAMPLE 6

Stability of Selectfluor™ Fluorinating Agent in CH₃OH/H₂O Solution

A saturated solution of commercial grade Selectfluor™ Fluorinating Agent, 1-chloromethyl-4-fluoro,-1,4-diazoniabicyclo[2.2.2]octane bis(tetrafluoroborate), was prepared by dissolving 9.00 g in 45.81 g of a 50:50 (v/v) mixture of CH₃OH/H₂O and stored at ambient temperature in a Nalgene polyethylene bottle. The "F⁺" activity was measured initially within 1 day of preparation, and then again after 7, 15, 21, and 29 days at room temperature. The results are given in Table 6.

TABLE 6

Results of Iodometric Analysis of a
CH₃OH/H₂O Solution of Selectfluor ™

| Days since Prepared | "F⁺" titer mmol/mL | % change[a] |
|---|---|---|
| within 1 day | 0.14 | initial |
| 7 days | 0.11 | 21.4 |
| 15 days | 0.10 | 28.6 |
| 21 days | 0.09 | 35.7 |
| 29 days | 0.09 | 35.7 | footnote
[a]Indicates percent change since initial measurement. A positive change is assigned a "0" value.

EXAMPLE 7

Stability of Intermediate to Selectfluor™ Fluorinating Agent in CH₃CN/H₂O Solution To a saturated solution of commercially produced intermediate to the Selectfluor™ Fluorinating Agent, 1-chloromethyl4-fluoro-1,4-diazoniabicyclo[2.2.2]octane fluoride tetrafluoroborate, in acetonitrile (solution contained 22.5 wt. % solids) was; added 7.49 g of deionized H₂O. The resulting homogeneous solution was stored at ambient temperature in a Nalgene polyethylene bottle. The "F⁺" activity was measured initially within I day of preparation, and then again after 8, 16, 22, and 28 days at room temperature. The results are given in Table 7.

TABLE 7

Iodometric Analysis of an CH₃CN/H₂O
Solution of Selectfluor ™ Intermediate

| Days since Prepared | "F⁺" titer mmol/mL | % change[a] |
|---|---|---|
| within 1 day | 0.34 | initial |
| 8 days | 0.27 | 20.6 |
| 16 days | 0.22 | 35.3 |
| 22 days | 0.16 | 52.9 |
| 28 days | 0.14 | 58.8 | footnote
[a]Indicates percent change since initial measurement. A positive change is assigned a "0" value.

EXAMPLE 8

Stability of Accufluor™ (NFPy) Fluorinating Agent in Aqueous Solution

A solution of commercial grade Accufluor™ Fluorinating Agent (NFPy), 1-fluoro-pyridinium pyridine heptafluorodiborate, was prepared by dissolving 11.02 g in 43.38 g of deionized H₂O. This sample was stored at ambient temperature in a Nalgene polyethylene bottle. The "F⁺" activity was measured initially within 1 day of preparation, and then again after 8, 16, 22, and 28 days at room temperature. The results are given in Table 8.

TABLE 8

Results of Iodometric Analysis of an
Aqueous Solution of Selectfluor ™ (NFPy)

| Days since Prepared | "F+" titer mmol/mL | % change[a] |
|---|---|---|
| within 1 day | 0.44 | initial |
| 8 days | 0.18 | 59.1 |
| 16 days | 0.10 | 77.3 |
| 22 days | 0.04 | 90.9 |
| 28 days | 0.02 | 95.5 | footnote
[a]Indicates percent change since initial measurement. A positive change is assigned a "0" value.

EXAMPLE 9

Stability of NFPTFB Fluorinating Agent in Aqueous Solution

A solution of commercial grade NFPTFB Fluorinating Agent, 1-fluoro-pyridinium tetrafluoroborate, was prepared by dissolving 5.01 g in 65.90 g of deionized $H_2O$. This sample was stored at ambient temperature in a Nalgene polyethylene bottle. The "F+" activity was measured initially within 1 day of preparation, and then again after 8, 16, 22, and 28 days at room temperature. The results are given in Table 9.

TABLE 9

Results of Iodometric Analysis of an Aqueous Solution of NFPTFB

| Days since Prepared | "F+" titer mmol/mL | % change[a] |
|---|---|---|
| within 1 day | 0.22 | initial |
| 8 days | 0.07 | 68.2 |
| 16 days | 0.03 | 86.4 |
| 22 days | 0.01 | 95.5 |
| 28 days | 0.01 | 95.5 | footnote
[a]Indicates percent change since initial measurement. A positive change is assigned a "0" value.

EXAMPLE 10

Stability of NFPT Fluorinating Agent in Aqueous Solution

A solution of commercial grade NFPT Fluorinating Agent, 1-fluoro-pyndinium triflate, was prepared by dissolving 6.26 g in 48.31 g of deionized $H_2O$. This sample was stored at ambient temperature in a Nalgene polyethylene bottle. The "F+" activity was measured initially within 1 day of preparation, and then again after 8, 16, 22, and 28 days at room temperature. The results are given in Table 10.

TABLE 10

Results of Iodometric Analysis of an Aqueous Solution of NFPT

| Days since Prepared | "F+" titer mmol/mL | % change[a] |
|---|---|---|
| within 1 day | 0.19 | initial |
| 8 days | 0.07 | 63.2 |
| 16 days | 0.02 | 89.5 |
| 22 days | 0.01 | 94.7 |
| 28 days | 0.01 | 94.7 | footnote
[a]Indicates percent change since initial measurement. A positive change is assigned a "0" value.

EXAMPLE 11

Stability of NFPDCTFB Fluorinating Agent in Aqueous Solution

A solution of commercial grade NFPDCTFB Fluorinating Agent, 1-fluoro-2,6-dichloropyridinium tetrafluoroborate, was prepared by dissolving 6.45 g in 49.27 g of deionized $H_2O$. This sample was stored at ambient temperature in a Nalgene polyethylene bottle. The "F+" activity was measured initially within 1 day of preparation, and then again after 8, 16, 22, and 28 days at room temperature. The results are given in Table 11.

TABLE 11

Results of Iodometric Analysis of an Aqueous Solution of NFPDCTFB

| Days since Prepared | "F+" titer mmol/mL | % change[a] |
|---|---|---|
| within 1 day | 0.20 | initial |
| 8 days | 0.19 | 5.0 |
| 16 days | 0.19 | 5.0 |
| 22 days | 0.17 | 15.0 |
| 28 days | 0.16 | 20.0 | footnote
[a]Indicates percent change since initial measurement. A positive change is assigned a "0" value.

EXAMPLE 12

Stability of SynFluor™ Fluorinating Agent in Aqueous Solution

An attempt was made to prepare an aqueous solution of commercial grade SynFluor™ Fluorinating Agent, 1,1'-difluoro-2,2'-bipyridinium bis(tetrafluoroborate), by mixing 9.27 g with 49.22 g of deionized $H_2O$. However, upon mixing the two components a violent and highly exothermic reaction occurred resulting in heating of the solution to the point that the plastic mixing vessel could not be held with the bare hand. After 1 minute, the sample had completely solidified into a brown mass. The "F+" activity of this brown mass indicated that all of the fluorinating ability had been depleted.

EXAMPLE 13

Assessing the Stability of Aqueous Solutions of Electrophilic Fluorination Agents by Thermal Analysis in a Closed System The stability of electrophilic fluorination agents in solution can also be assessed by measuring the thermal properties of the solutions under various conditions. In this example, the thermal properties of the aqueous solutions were measured using the Radex-Solo Thermal Hazards Screening System (Radex). This instrumental method of analysis provides a heat flux related signal as well as a pressure measurement in a closed cell apparatus.

To assess the thermal properties of the fluorination agents in aqueous solution, a nitrogen head pressured of about 85 psig was used in the closed cell in order to suppress the endothermic boiling of water. Therefore, the data obtained from this particular analysis provides a measure of the total potential heat (on a weight-of-contained material basis) that could be evolved (without any heat absorption due to evaporation of water) if the solutions containing the fluorination agents were allowed to heat to the onset of decomposition and then continue to heat to complete thermal decomposition of the contained fluorination agent.

In Table 13 the results of the Radex measurements on aqueous solutions of Selectfluor™, Accufluor™, NFQT, and the intermediate to Selectfluor™ called FTEDA(F)(BF$_4$) are given. These data are depicted graphically in FIG. 1.

TABLE 13

Results for Radex Measurements on Aqueous Solutions of Various Electrophilic Fluorination Agents

| "F$^+$" Agent | Sample Wt. (g) | Exotherm Onset$^a$ (° C.) | Measured Heat (J/g) | Normalized Heat$^b$ (J/g) |
|---|---|---|---|---|
| Selectfluor ™ | 0.68 | 108 | 140 | 367 |
| Selectfluor ™ | 1.05 | 83 | 115 | 301 |
| Accufluor ™ | 1.16 | 83 | 527 | 429 |
| NFQT | 1.02 | 136 | 91 | 171 |
| FTEDA (F)(BF$_4$) | 1.17 | 62 | 36 | 133 |
| FTEDA (F)(BF$_4$) | 3.03 | 85 | 54 | 199 | footnotes:
$^a$Is the temperature at which exothermic decomposition begins.
$^b$Normalized heat is the heat given off per gram of the aqueous solution normalized to 1M concentration.

From the data in Table 13 it is apparent that the aqueous solution containing FTEDA (F)(BF$_4$) is the least stable of those measured since its onset temperature for thermal decomposition is the lowest. Selectfluor™ and Accufluor™ are approximately equivalent, whereas NFQT is the most stable displaying the highest onset temperature.

Figure 2:
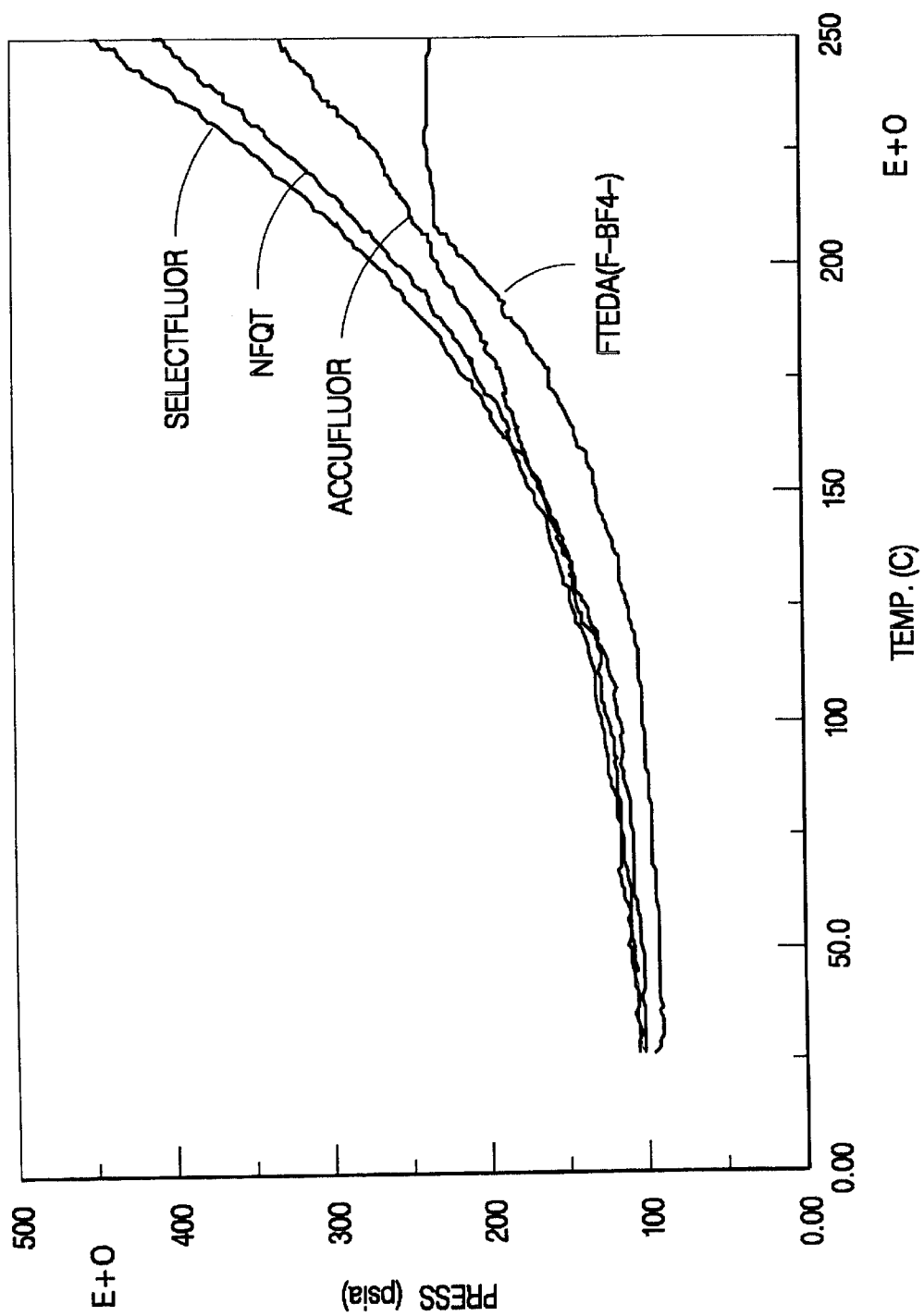
FIG. 2 is a graph of pressure in psig as temperature is ramped in degrees celsius for several fluorinating agents.
Figure 3:
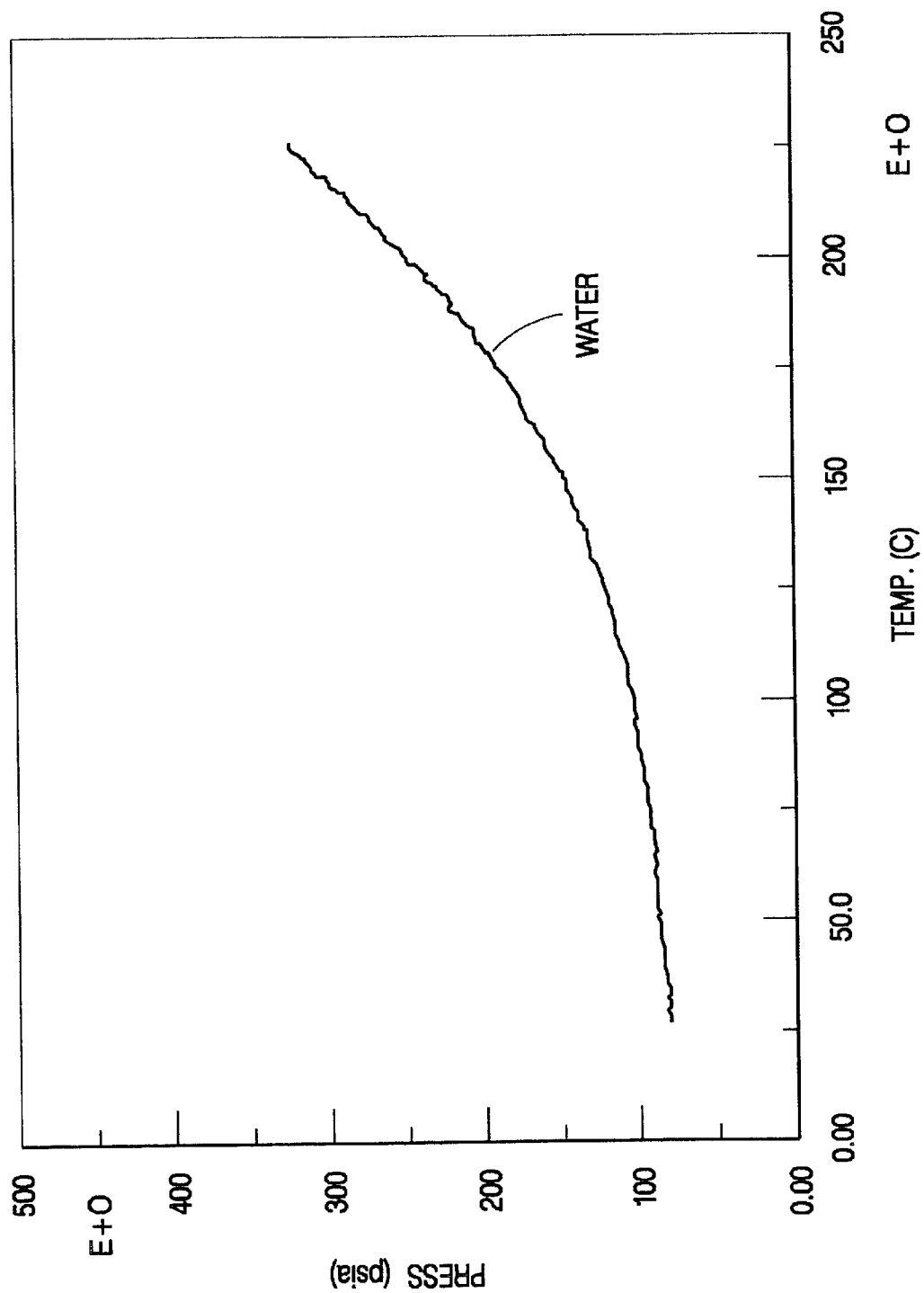
FIG. 3 is a graph of pressure in psig as temperature is ramped in degrees celsius for water as a comparison to the effects recorded in FIG. 2 for fluorinating agents.

In FIG. 2, an overlay plot of the pressure versus temperature data corresponding to the Radex measurements summarized in Table 13 is given. FIG. 3 is provided for comparison and depicts a plot of pressure versus temperature for pure water. Upon comparison of the two plots, it is evident from the curve shapes that there is no substantial increase in system pressure during decomposition of the "F$^+$" compounds and in fact, the pressure curves simply increase commensurate with the increase in vapor pressure of water with increasing temperature.

EXAMPLE 14

Assessing the Stability of Aqueous Solutions of Electrophilic Fluorination Agents by Thermal Analysis in an Open System To assess the thermal stability of the fluorination agents in aqueous solution under a simulated decomposition in a vented container, Radex measurements on aqueous solutions of Selectfluor™, Accufluor™, NFQT, and the intermediate to Selectfluor™ called FTEDA (F)(BF$_4$) were done in an open cell. In this analysis the samples were heated at a rate of 2° C. per minute from ambient temperature to 350° C. in an open cell, resulting in decomposition of the fluorination agent and complete evaporation of all water. The data obtained from this particular analysis provides a measure of the total net heat flux for a given fluorination agent in aqueous solution and represents the sum of the exothermic heat of decomposition of the fluorination agent and the endothermic heat due to evaporation of water (latent heat= 2,259 J/g at 100° C.) as the sample is allowed to heat to the onset of decomposition and then continue to heat to complete thermal decomposition of the contained fluorination agent. The data from these measurements are summarized in Table 14.

TABLE 14

Results for Radex Measurements on Aqueous Solutions of Various Electrophilic Fluorination Agents

| "F$^+$" Agent | Sample Wt. (g) | Measured Heat (J/g) |
|---|---|---|
| Selectfluor ™ | 2.52 | −1094 |
| Accufluor ™ | 2.51 | −498 |
| NFQT | 2.52 | −1262 |
| FTEDA (F)(BF$_4$) | 2.51 | −358 |

In Table 14 the "Measured Heat" expressed in Joules per gram of sample is the net heat measured during the experiment; a negative number indicates a net endothermic process whereas a positive number indicates a net exothermic process. From the data in Table 14 it is apparent for each of the "F$^+$" agents in aqueous solution, that the heat uptake or absorption due to boiling and vaporization of water surpasses any exothermic heat dissipation which may be evolved due to decomposition of the "F$^+$" agent and thus each of the measured heat values are a negative number. The net effect of heating these aqueous solutions is endothermic. In other words, the presence of water has a profound "quenching" effect which overwhelms any exothermic processes which may initiate. These aqueous solutions are safe with respect to self-accelerating decomposition up to 350° C. and until all of the water evaporates.

There is a maximum value of fluorination agent concentration above which the exothermic heat of decomposition of the fluorination agent surpasses the endothermic effect of the evaporating solvent, and it is this maximum fluorination agent concentration which establishes the safe upper limit of the present invention. In the specific case of Selectfluor™, the total heat of decomposition for the pure compound has been measured by Differential Scanning Calorimetry (DSC) yielding a value of 977 Joules of heat evolved per gram of solid decomposed. If one uses this value in combination with the literature value for the latent heat of vaporization (the amount of heat removed due to evaporation) for pure H$_2$O of −2259 J/g, an algebraic relationship can be established as follows:

$$\text{exothermic heat of decomposition} + \text{endothermic heat of evaporation} = \text{net observed heat} \quad (1)$$

substituting 977 J/g for the exothermic heat of decomposition and −2259 J/g for the latent heat of vaporization for pure H$_2$O, the equation for net heat observed for any mixture containing x% fluorination agent and (1−x)% H$_2$O becomes:

$$977x + (1-x)(-2259) = \text{net heat observed} \quad (2)$$

To establish the maximum concentration of fluorination agent in H$_2$O that will produce a zero net heat observed one need only solve for x; therefore:

$$977x + 2259x - 2259 = 0 \quad (3)$$

$$\therefore 3236x - 2259 = 0 = \text{net heat observed} \quad (4)$$

$$\therefore 3236x = 2259 \text{ and } x = 0.70$$

if x>0.70
substituting x=0.71 info eq 4 one gets:

$$3236(0.71)-2259=38.56 \text{ J/g}$$

since the net heat is a positive value, this indicates that the system will show net heat evolved.
if x<0.70
substituting x=0.69 into eq 4 one gets:

$$3236(0.69)-2259 =-26.16 \text{ J/g}$$

since the net heat is a negative value, this indicates that the system will show net heat absorbed.

Therefore, in general, any mixture of Selectfluor™ in $H_2O$ containing less than 70 weight percent fluorination agent will provide a safe medium wherein even during a heating event, the system is protected from "runaway" heating due to the endothermic cooling affect of the solvent. Alternatively, any mixture of Selectfluor™ in $H_2O$ containing more than 70 weight percent fluorination agent will provide a medium wherein during a heating event, the system could potentially exhibit "runaway" heating due to the exothermicity of the decomposing solid fluorination agent.

One can repeat the above calculations for different solvents and different fluorination agents provided the latent heat of vaporization and heat of decomposition values, respectively, are known, and these values can be substituted into eq 5 below:

$$x(\text{heat of decomposition})+(1-x)(\Delta H \text{ Vaporization})=\text{net observed heat} \quad (5)$$

For Selectfluor™, using the heat of decomposition of 977 J/g, a number of solvents have been used to calculate the maximum concentration value (value x in eq 5) for the fluorination agent in a particular solvent and these results are summarized in Table 15.

TABLE 15

Maximum Concentration of Selectfluor ™ in Various Solvents that will Produce a Zero Net Heat Observed

| Solvent | ΔH Vaporization J/g | Maximum Value of "x" from eq 5 values are x% by wt. |
|---|---|---|
| acetonitrile | −745 | 43% |
| methanol | −1075 | 52% |
| ethanol | −841 | 46% |
| methylene chloride | −331 | 25% |

For Accufluor™, using the heat of decomposition of 1,452 J/g (average value of triplicate analysis by DSC), a number of solvents have been used to calculate the maximum concentration value (value x in eq 5) for the fluorination agent in a particular solvent and these results are summarized in Table 16.

TABLE 16

Maximum Concentration of Accufluor ™ in Various Solvents that will Produce a Zero Net Heat Observed

| Solvent | ΔH Vaporization J/g | Maximum Value of "x" from eq 5 values are x% by wt. |
|---|---|---|
| water | −2,259 | 60% |
| acetonitrile | −745 | 33% |

TABLE 16-continued

Maximum Concentration of Accufluor ™ in Various Solvents that will Produce a Zero Net Heat Observed

| Solvent | ΔH Vaporization J/g | Maximum Value of "x" from eq 5 values are x% by wt. |
|---|---|---|
| methanol | −1075 | 42% |
| ethanol | −841 | 36% |
| methylene chloride | −331 | 18% |

As noted above, there is a general need in the industry for a safe and efficient means of storing, transporting and delivering electrophilic fluorination agents primarily because of the sensitivity of these agent to thermal degradation and also due to slow loss of "$F^+$" activity in the solid undiluted form at ambient conditions.

Examples 1–5 illustrate the remarkable stability of three different quaternary (containing the +N-F moiety) electrophilic fluorination agents, Selectfluor™, Accufluor™, and NFQT, in aqueous and aqueous/organic solvents. Examples 6–12 are comparative examples which provide evidence for instability of various electrophilic fluorinating agents in aqueous and aqueous/organic media. Specifically, Example 6 illustrates that Selectfluor™ is not as stable in methanol/water as it is in water alone or in methanol/acetonitrile. Example 7 illustrates that the intermediate to Selectfluor™, which differs from Selectfluor™ only by the presence of a fluoride ion ($F^-$) in place of a tetrafluoroborate ion ($BF_4^-$), is much less stable in water/acetonitrile solvent than is Selectfluor™. Examples 8–12 illustrate that various pyridinium-based electrophilic fluorination agents are very unstable in aqueous solution and even the most stable of these, NFPT, degrades very rapidly in aqueous solution.

Whereas Examples 1–12 evaluate the stability and instability of electrophilic fluorination agents in aqueous and aqueous/organic solvent systems in terms of the preservation or loss of "$F^+$" activity, Examples 13 and 14 provide evidence apart from the preservation of "$F^+$" activity for the stability and inherent safety of electrophilic fluorination agents which are contained in aqueous solution. The data in Examples 13 and 14 say nothing of the "$F^+$" activity, but rather demonstrate that these solutions are safe with respect to thermal runaway reactions or self accelerating decomposition reactions.

The value of the present invention is that it provides an economical means of safely "containing" or "packaging" these commercial electrophilic fluorination agents whereby these agents are readily stored and transported in this package and in a form which is readily and directly useable, i.e., in solution, and in some instances without loss of "$F^+$" activity. Moreover, these solutions can be mixtures of water and organic solvent, such that the customer can use the solutions directly in their fluorination processes without further modification. Most importantly, the solution medium provides a tremendous safety margin for storage and transportation, since the solution medium has an enormous ability lo absorb heat (due to the latent heat of vaporization of the liquid) relative to the contained active fluorination agent.

The present invention has been set forth with regard to several preferred embodiments, however, the full scope of the present invention should be ascertained from the claims which follow.

What is claimed is:
1. A package for the safe containment of a quaternary nitrogen electrophilic fluorination agent, comprising:
   a container, having at least one sealable orifice, and containing:

a) a quantity of said quaternary nitrogen electrophilic fluorination agent; and
b) a solvent in liquid phase under ambient conditions and compatible with said quaternary nitrogen electrophilic fluorination agent, in sufficient quantity to absorb the heat of decomposition of said quantity of said quaternary nitrogen electrophilic fluorination;

wherein a maximum quantity of said quaternary nitrogen electrophilic fluorination agent in said container is determined by the equation:

$$x \cdot (\text{heat of decomposition of fluorination agent}) + (1-x) \cdot (\text{latent heat of vaporization of solvent}) = 0,$$

wherein x·100 is the weight % of said quaternary nitrogen electrophilic fluorination agent and (1−x)·100 is the weight % of said solvent.

2. The package of claim 1 wherein said quaternary nitrogen electrophilic fluorination agent is selected from the group consisting of: 1-chloromethyl-4-fluoro-1,4-diazoniabicyclo[2.2.2]octane bis(tetrafluoroborate); 1-chloromethyl-4-fluoro-1,4-diazoniabicyclo[2.2.2]octane fluoride (tetrafluoroborate); 1-fluoro4-hydroxy-1,4-diazoniabicyclo[2.2.2]octane bis(tetrafluoroborate); 1-fluoro-4-methyl-1,4-diazoniabicyclo[2-2-2]octane bis (tetrafluoroborate); N-fluoro-quinuclidinium triflate; 1-fluoro-pyridinium pyridine heptafluorodiborate; 1-fluoro-pyridinium tetrafluoroborate; 1-fluoro-pyridinium triflate; 1-fluoro-2,6-dichloropyridinium tetrafluoroborate; 1,1'-difluoro-2,2'-bipyridinium bis(tetrafluoroborate) and mixtures thereof.

3. The package of claim 1 wherein said quaternary nitrogen electrophilic fluorination agent is selected from the group consisting of: 1-chloromethyl-4-fluoro-1,4-diazoniabicyclo[2.2.2]octane bis(tetrafluoroborate); 1-chloromethyl4-fluoro-1,4-diazoniabicyclo[2.2,.2]octane fluoride (tetrafluoroborate); 1-fluoro4-hydroxy-1,4-diazoniabicyclo[2.2.2]octane bis(tetrafluoroborate); 1-fluoro-4-methyl-1, 4-diazoniabicyclo[2-2-2]octane bis (tetrafluoroborate); N-fluoro-quinuclidinium triflate and mixtures thereof and said solvent is water.

4. The package of claim 1 wherein said solvent includes an organic solvent.

5. The package of claim 1 wherein said organic solvent is selected from the group consisting of: acetonitrile, propionitrile, methanol, ethanol, propanol, isopropanol, N,N-dimethylformamide, tetrahydrofuran, ethyl ether, aromatic hydrocarbon of $C_{u-v}$, halogenated hydrocarbon of $C_{w-x}$, and perfluorinated hydrocarbon of $C_{y-z}$ where u=3, v=10, w=1, x=8, y=1 and z=8.

6. The package of claim 1 wherein said solvent is a mixture of acetonitrile and methanol.

7. The package of claim 1 wherein said quaternary nitrogen electrophilic fluorination agent is 1-chloromethyl-4-fluoro-1,4-diazoniabicyclo[2.2.2]octane bis (tetrafluoroborate) and said solvent is water.

8. The package of claim 1 wherein said solvent is at least 30 wt. % water, and an organic solvent selected from the group consisting of: acetonitrile; tetrahydrofuran; N,N-dimethylformamide and mixtures thereof.

9. The package of claim 1 wherein said quaternary nitrogen electrophilic fluorination agent is 1-chloromethyl-4-fluoro-1,4-diazoniabicyclo[2.2.2]octane bis (tetrafluoroborate) and said solvent is acetonitrile and methanol.

10. The package of claim 1 wherein said quaternary nitrogen electrophilic fluorination agent is 1-fluoro-4-hydroxy-1,4-diazoniabicyclo[2.2.2]octane bis (tetrafluoroborate) and said solvent is water.

11. The package of claim 1 wherein said solvent is at least 40 wt. % water, and an organic solvent selected from the group consisting of: acetonitrile; tetrahydrofuran; N,N-dimethylformamide and mixtures thereof.

12. The package of claim 1 wherein said quaternary nitrogen electrophilic fluorination agent is N-fluoroquinuclidinium triflate and said solvent is water.

13. The package of claim 1 wherein said solvent is water, and an organic solvent selected from the group consisting of acetonitrile; tetrahydrofuran; N,N-dimethylformamide and mixtures thereof.

14. The package of claim 1 wherein said quaternary nitrogen electrophilic fluorination agent is selected from the group consisting of: 1-fluoro-pyridinium pyridine heptafluorodiborate; 1-fluoro-pyridinium tetrafluoroborate; 1-fluoro-pyridinium triflate; 1-fluoro-2,6-dichloropynridinium tetrafluoroborate; 1,1'-difluoro-2,2'-bipyridinium bis (tetrafluoroborate) and mixtures thereof and said solvent is an organic solvent.

* * * * *